United States Patent
Barbagli

(10) Patent No.: US 12,086,284 B2
(45) Date of Patent: Sep. 10, 2024

(54) SYSTEMS AND METHODS FOR CENSORING CONFIDENTIAL INFORMATION

(71) Applicant: Intuitive Surgical Operations, Inc., Sunnyvale, CA (US)

(72) Inventor: Federico Barbagli, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 740 days.

(21) Appl. No.: 17/258,074

(22) PCT Filed: Jul. 10, 2019

(86) PCT No.: PCT/US2019/041205
§ 371 (c)(1),
(2) Date: Jan. 5, 2021

(87) PCT Pub. No.: WO2020/014360
PCT Pub. Date: Jan. 16, 2020

(65) Prior Publication Data
US 2021/0200900 A1   Jul. 1, 2021

Related U.S. Application Data

(60) Provisional application No. 62/696,211, filed on Jul. 10, 2018.

(51) Int. Cl.
| G06F 21/62 | (2013.01) |
| G16H 10/60 | (2018.01) |
| G16H 40/67 | (2018.01) |

(52) U.S. Cl.
CPC ......... *G06F 21/6245* (2013.01); *G16H 10/60* (2018.01); *G16H 40/67* (2018.01)

(58) Field of Classification Search
CPC ..... G06F 21/6245; G16H 10/60; G16H 40/67
See application file for complete search history.

(56) References Cited

U.S. PATENT DOCUMENTS 8,836,530 B1 * 9/2014 Bowers ................... G06F 21/32
340/687
9,591,481 B1 * 3/2017 Fisher .................. H04B 7/0413
(Continued)

FOREIGN PATENT DOCUMENTS

| CN | 105718770 A | 6/2016 |
| CN | 104298902 B | 9/2017 |

OTHER PUBLICATIONS

International Search Report and Written Opinion for Application No. PCT/US2019/041205, mailed on Nov. 6, 2019, 13 pages (ISRG10110/PCT).

(Continued)

*Primary Examiner* — James R Turchen
(74) *Attorney, Agent, or Firm* — Haynes & Boone, LLP

(57) ABSTRACT

A method and apparatus for censoring selected information. A mobile device is registered with a medical system. The medical system includes a display device. A trigger is received from the mobile device at the medical system. A display on the display device is modified in response to the received trigger. Selected information in the display is censored in the modified display. Alternatively, an image of a display on the display device is generated with selected information censored in response to receiving the trigger. The image of the display with the selected information censored is sent to the mobile device.

20 Claims, 10 Drawing Sheets

(56) References Cited

U.S. PATENT DOCUMENTS

| | | | | |
|---|---|---|---|---|
| 9,626,493 | B2* | 4/2017 | Cohen | G06F 21/10 |
| 10,382,620 | B1* | 8/2019 | Allen | H04M 1/72463 |
| 10,929,561 | B2* | 2/2021 | Long | G06V 40/161 |
| 2004/0078238 | A1* | 4/2004 | Thomas | G16H 10/60 |
| | | | | 705/3 |
| 2004/0148197 | A1* | 7/2004 | Kerr | G06F 21/84 |
| | | | | 705/2 |
| 2006/0056670 | A1* | 3/2006 | Hamadeh | G06T 7/0002 |
| | | | | 382/128 |
| 2008/0208579 | A1* | 8/2008 | Weiss | G06Q 30/02 |
| | | | | 707/E17.014 |
| 2014/0351175 | A1* | 11/2014 | Venkat | H04W 4/029 |
| | | | | 706/46 |
| 2016/0157803 | A1* | 6/2016 | Keller | A61B 5/6852 |
| | | | | 600/467 |
| 2016/0379010 | A1* | 12/2016 | Farkash | G06F 21/6245 |
| | | | | 726/1 |
| 2017/0068829 | A1* | 3/2017 | Shaw | G06F 21/50 |
| 2019/0020676 | A1* | 1/2019 | Laughlin | H04L 63/1441 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, Nj, USA 1986, vol. 3A, 332 pages.
International Preliminary Report on Patentability for Application No. PCT/2019/041205, mailed on Jan. 21, 2021, 08 p. (P00874-WO).

* cited by examiner

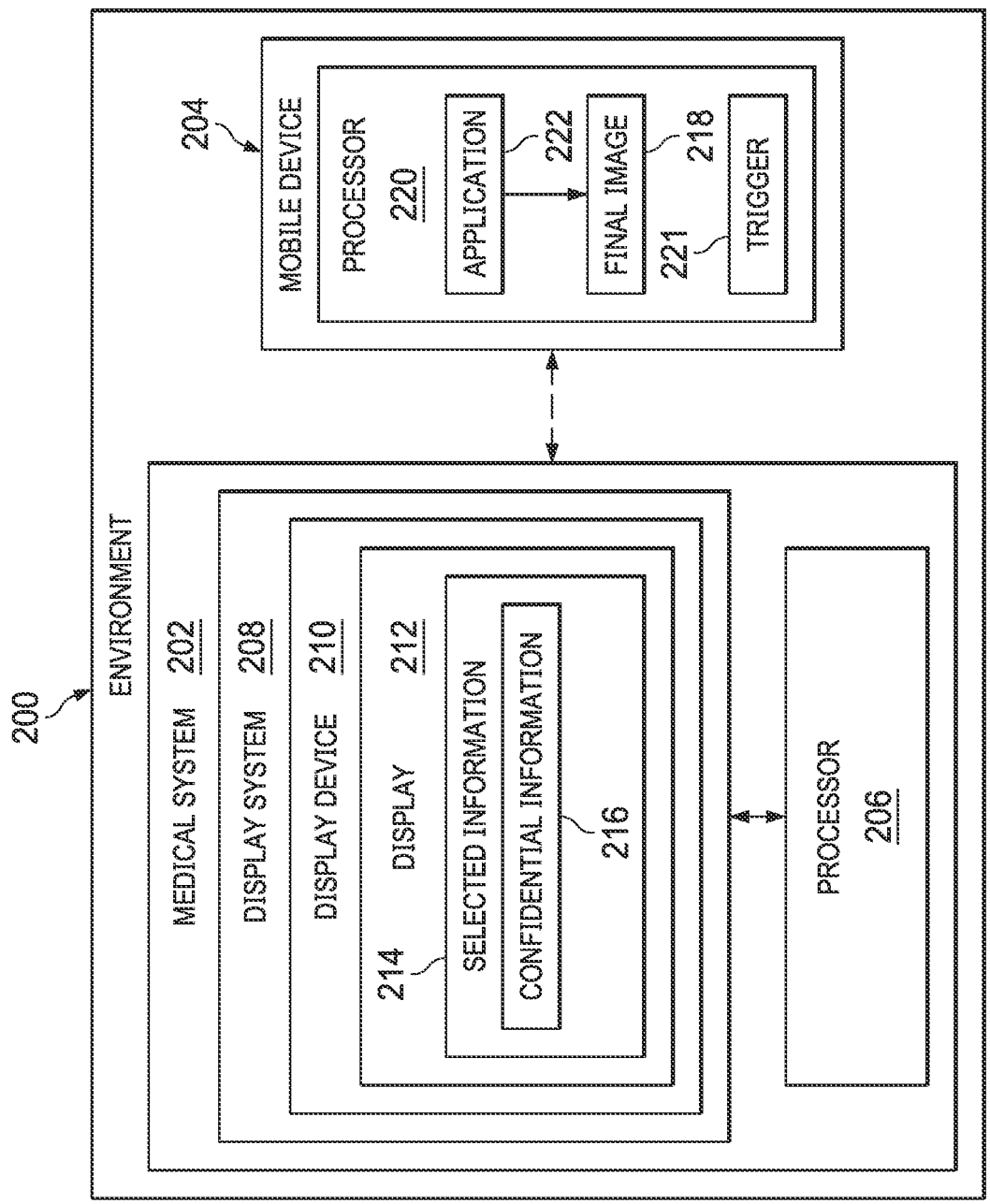

SYSTEMS AND METHODS FOR CENSORING CONFIDENTIAL INFORMATION

CROSS-REFERENCE TO RELATED APPLICATIONS

This application is the U.S. national phase of International Application No. PCT/US2019/041205, filed Jul. 10, 2019, which designates the U.S. and claims priority to and the benefit of U.S. Provisional Application No. 62/696,211, filed Jul. 10, 2018, both of which are incorporated by reference herein in their entirety.

FIELD

The present disclosure is directed to systems and methods for protecting confidential information. More particularly, the present disclosure is directed to systems and methods for generating images in which selected information has been censored.

BACKGROUND

Various medical procedures may be performed on different patients in an operating room or other environment. During a medical procedure, one or more display devices located within the operating room may present information to the one or more clinicians performing the medical procedure as well as other personnel who are present within the operating room. A display device may present, for example, information about the medical procedure being performed, information about the patient on whom the medical procedure is being performed, images of the patient provided by endoscopic instruments, other information, or a combination thereof. In certain situations, confidential patient information is presented on the display device.

As one example, a teleoperational system may be used to operate minimally invasive medical tools to perform minimally invasive medical techniques. The minimally invasive medical tools may include imaging instruments, such as endoscopic instruments. A display device secured to or located near the teleoperational system may be used to display images provided by an endoscopic instrument. These images may be displayed in association with confidential information about the patient on whom the medical procedure is being performed. The confidential information may include, for example, the patient's name, the patient's date of birth, and the patient's identification number. Systems and methods for improving the protection of patient confidential information during and after a medical procedure are needed.

SUMMARY

The embodiments of the invention are summarized by the claims that follow the detailed description.

In one embodiment, a method for censoring selected information is provided. A mobile device is registered with a medical system. The medical system includes a display device. A trigger is received from the mobile device at the medical system. A display on the display device is modified in response to the received trigger. Selected information in the display is censored in the modified display.

In another embodiment, a method for censoring selected information is provided. A mobile device is registered with a medical system. The medical system includes a display device. A trigger is received from the mobile device at the medical system. An image of a display on the display device is generated with selected information censored in response to receiving the trigger. The image of the display with the selected information censored is sent to the mobile device.

In yet another embodiment, a medical system comprises a display device and a processor. The processor is configured to register a mobile device. The processor is configured to receive a trigger from the mobile device. The processor is configured to modify a display on the display device in response to the received trigger. Selected information is censored in the modified display.

In another embodiment, a method is provided for capturing a screenshot. Medical information received from a medical system is displayed on a display of a mobile device. A trigger is received from the mobile device to capture the displayed medical information. Selected information to be censored is identified in response to the received trigger. The screenshot of the display is generated with the selected information being censored in the screenshot.

In yet another embodiment, a mobile device a display and a processor. The processor is configured to display medical information received from a medical system in the display; receive a trigger to capture the displayed medical information; identify selected information to be censored in response to the received trigger; and generate a screenshot of the display, wherein the selected information is censored in the screenshot.

In still another embodiment, a method of obscuring selected information is provided. Medical information is displayed in a display on a display device of a medical system. A trigger is received from the mobile device at the medical system. A region of the display that presents the selected information is obscured in response to receiving the trigger such that an image of the display device includes the obscured region.

In another embodiment, a method for modifying a display on a display device of a medical system is provided. Medical information is displayed in the display on the display device of the medical system. A trigger is received from the mobile device at the medical system. Additional information is added on the display in response to receiving the trigger such that an image of the display device includes the additional information.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 2 is a schematic diagram of an environment, in accordance with an embodiment.

DETAILED DESCRIPTION

Figure 1A:
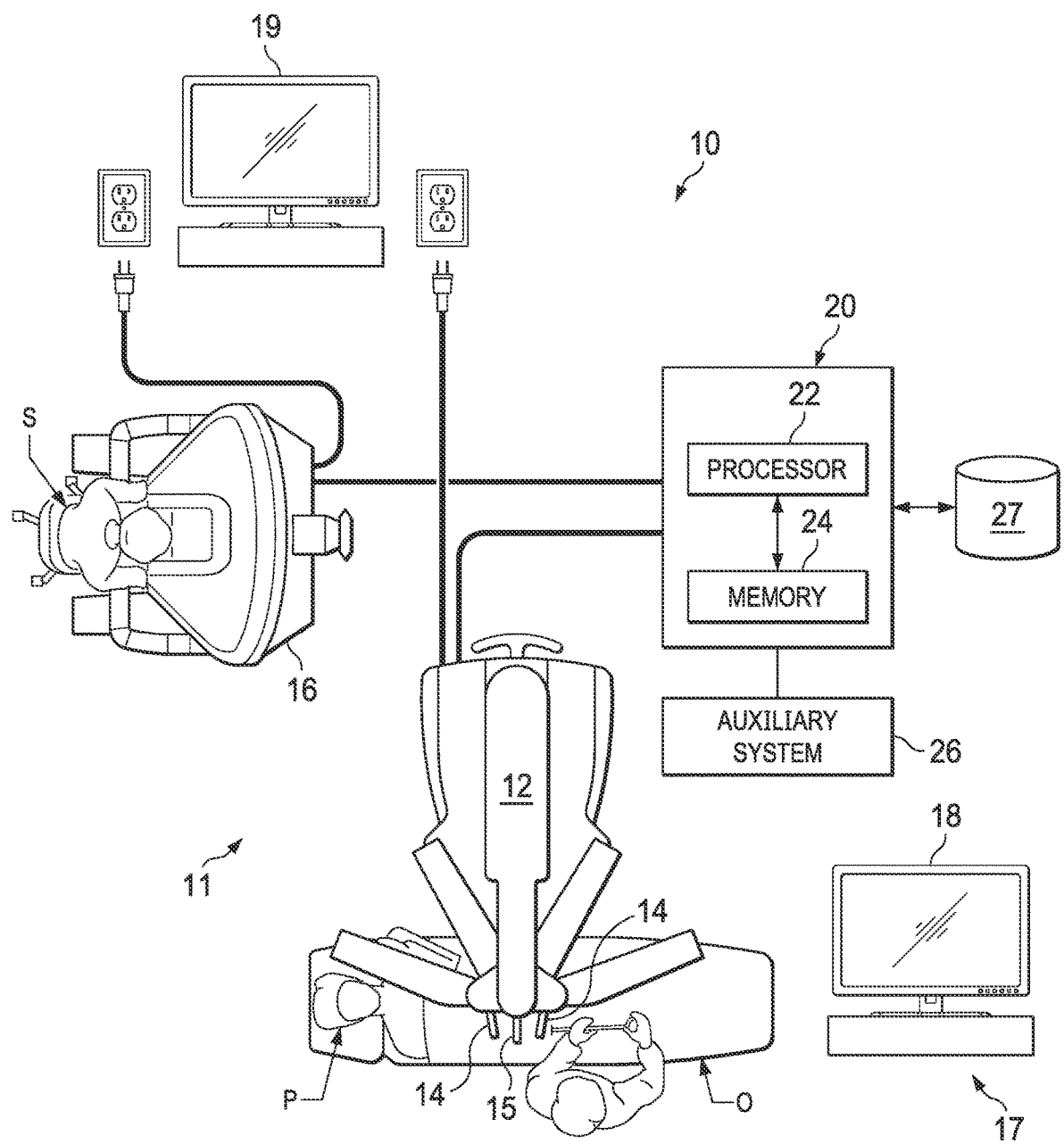
FIG. 1A is a schematic view of a medical system, in accordance with an embodiment.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, as would be appreciated by one skilled in the art, embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment may be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom).

Figure 1B:
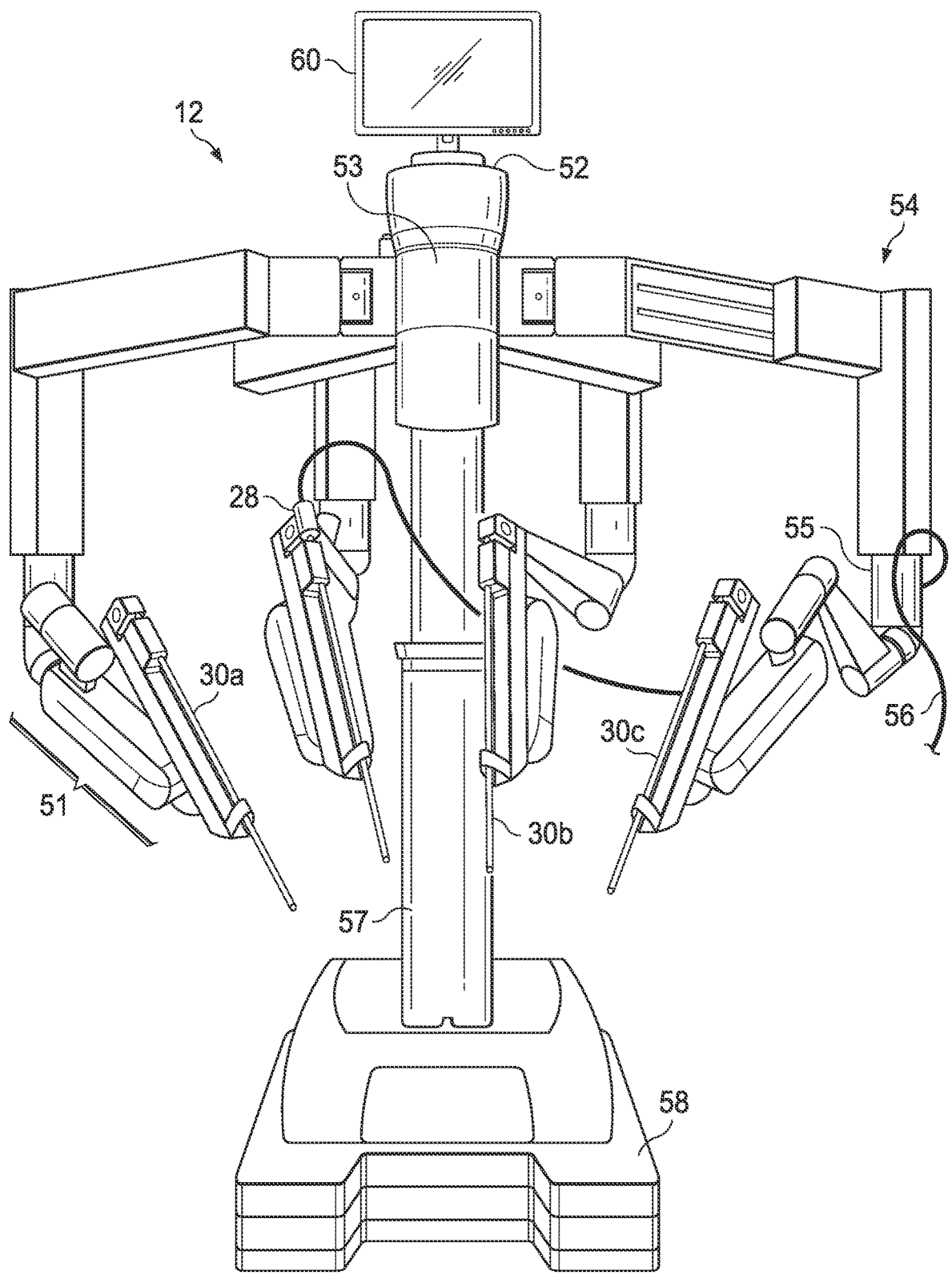
FIG. 1B is a perspective view of an assembly, in accordance with an embodiment.
Figure 1C:
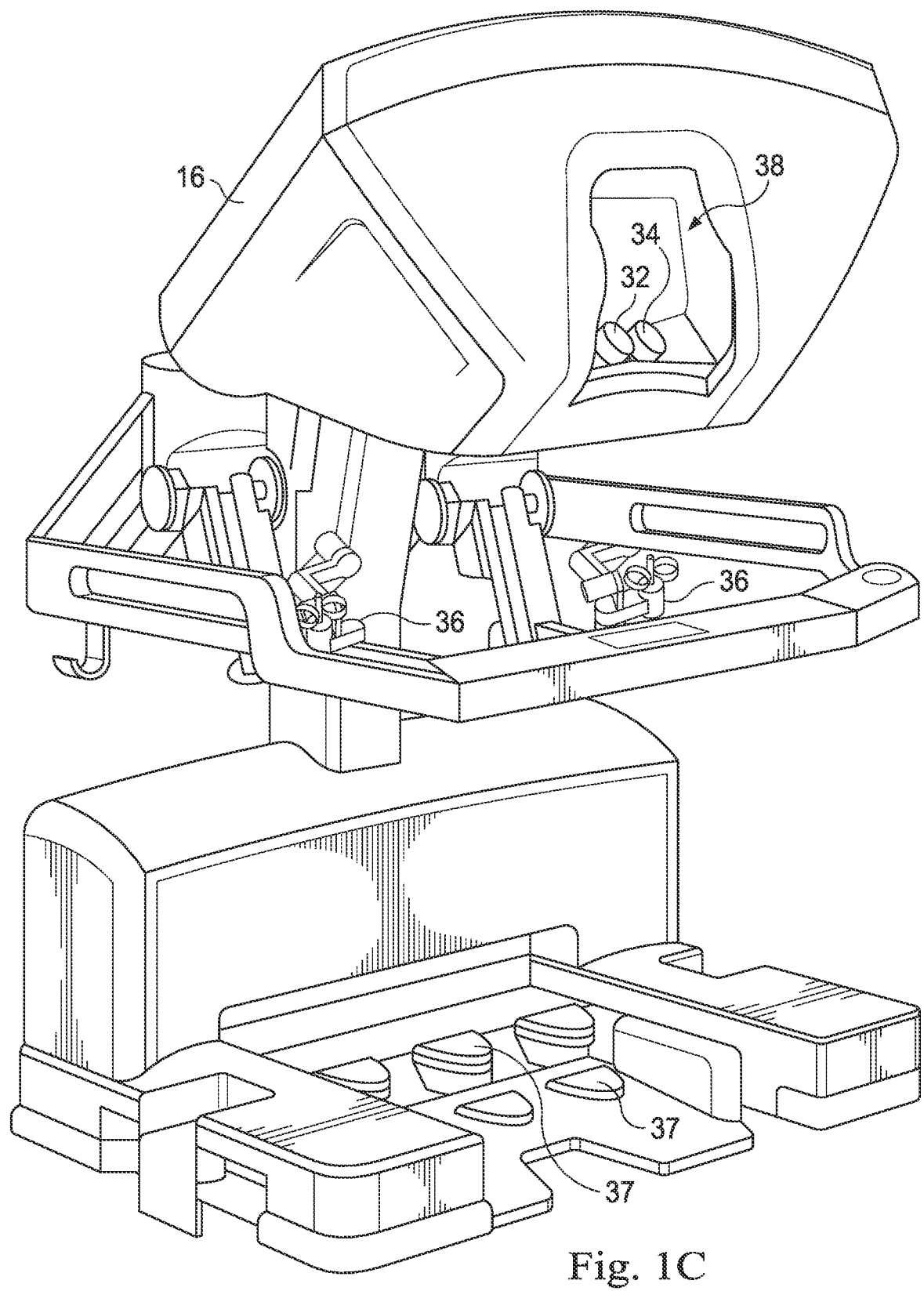
FIG. 1C is a perspective view of a surgeon's control console for a medical system, in accordance with an embodiment.
Figure 1D:
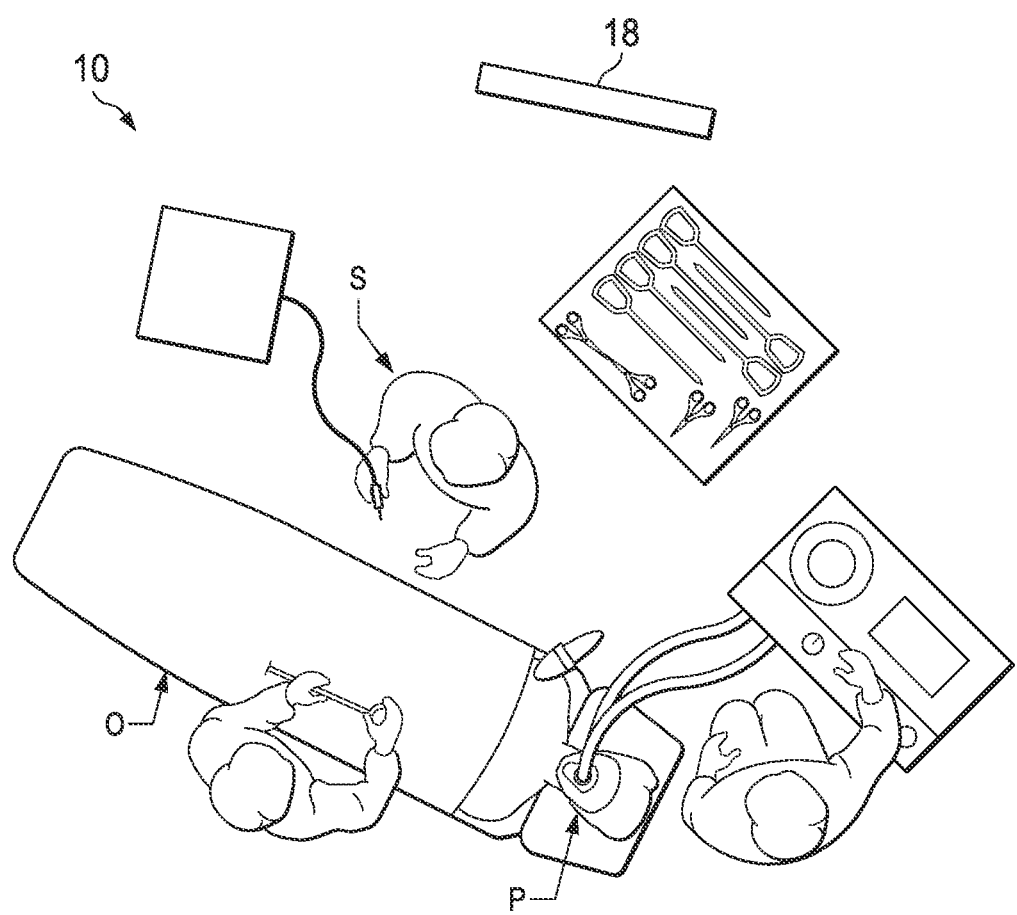
FIG. 1D is a top view of a different type of medical system, in accordance with an embodiment.

Referring now to the drawings, FIGS. 1A, 1B, and 1C together provide an overview of a medical system 10 that may be used in, for example, medical procedures including diagnostic, therapeutic, or surgical procedures. The medical system 10 is located in a surgical environment 11. The medical system 10 may take various forms. In one or more embodiments, the medical system 10 may be a teleoperational medical system that is under the teleoperational control of a surgeon. In alternative embodiments, the medical system 10 may be under the partial control of a computer programmed to perform the medical procedure or sub-procedure. In still other alternative embodiments, the medical system 10 may be a fully automated medical system that is under the full control of a computer programmed to perform the medical procedure or sub-procedure with the medical system 10. In still other alternative embodiments, the medical system 10 may be a fully manual medical system as shown in FIG. 1D below. One example of the medical system 10 that may be used to implement the systems and techniques described in this disclosure is the da Vinci® Surgical System manufactured by Intuitive Surgical, Inc. of Sunnyvale, California.

As shown in FIG. 1A, the medical system 10 generally includes an assembly 12, which may be mounted to or positioned near an operating table O on which a patient P is positioned. The assembly 12 may be referred to as a patient side cart, a surgical cart, or a surgical robot. In one or more embodiments, the assembly 12 may be a teleoperational assembly. The teleoperational assembly may be referred to as, for example, a teleoperational arm cart. A medical instrument system 14 and an endoscopic imaging system 15 are operably coupled to the assembly 12. An operator input system 16 allows a surgeon S or other type of clinician to view images of or representing the surgical site and to control the operation of the medical instrument system 14 and/or the endoscopic imaging system 15.

The medical instrument system 14 may comprise one or more medical instruments. In embodiments in which the medical instrument system 14 comprises a plurality of medical instruments, the plurality of medical instruments may include multiple of the same medical instrument and/or multiple different medical instruments. Similarly, the endoscopic imaging system 15 may comprise one or more endoscopes. In the case of a plurality of endoscopes, the plurality of endoscopes may include multiple of the same endoscope and/or multiple different endoscopes.

The operator input system 16 may be located at a surgeon's control console, which may be located in the same room as operating table O. In some embodiments, the surgeon S and the operator input system 16 may be located in a different room or a completely different building from the patient P. The operator input system 16 generally includes one or more control device(s) for controlling the medical instrument system 14. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and other types of input devices.

In some embodiments, the control device(s) will be provided with the same degrees of freedom as the medical instrument(s) of the medical instrument system 14 to provide the surgeon S with telepresence, which is the perception that the control device(s) are integral with the instruments so that the surgeon S has a strong sense of directly controlling instruments as if present at the surgical site. In other embodiments, the control device(s) may have more or fewer degrees of freedom than the associated medical instruments and still provide the surgeon S with telepresence. In some embodiments, the control device(s) are manual input devices that move with six degrees of freedom, and which may also include an actuatable handle for actuating instruments (for example, for closing grasping jaw end effectors, applying an electrical potential to an electrode, delivering a medicinal treatment, and actuating other types of instruments).

The assembly 12 supports and manipulates the medical instrument system 14 while the surgeon S views the surgical site through the operator input system 16. An image of the surgical site may be obtained by the endoscopic imaging system 15, which may be manipulated by the assembly 12. The assembly 12 may comprise endoscopic imaging systems 15 and may similarly comprise multiple medical instrument systems 14 as well. The number of medical instrument systems 14 used at one time will generally depend on the diagnostic or surgical procedure to be performed and on space constraints within the operating room, among other factors. The assembly 12 may include a kinematic structure of one or more non-servo controlled links (e.g., one or more links that may be manually positioned and locked in place, generally referred to as a set-up structure) and a manipulator. When the manipulator takes the form of a teleoperational manipulator, the assembly 12 is a teleoperational assembly. The assembly 12 includes a plurality of motors that drive inputs on the medical instrument system 14. In an embodiment, these motors move in response to commands from a control system (e.g., control system 20). The motors include drive systems which when coupled to the medical instrument system 14 may advance a medical instrument into a naturally or surgically created anatomical orifice. Other motorized drive systems may move the distal end of said medical instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors may be used to actuate an articulable end effector of the medical instrument for grasping tissue in the jaws of a biopsy device or the like. Medical instruments of the medical instrument system 14 may include end effectors having a single working member such as a scalpel, a blunt blade, an optical fiber, or an electrode. Other end effectors may include, for example, forceps, graspers, scissors, or clip appliers.

The medical system 10 also includes at least one display system 17. The display system 17 may include at least one display device. In one or more embodiments, the display system 17 includes a display device 18 and a display device 19, which present information about the medical procedure performed using assembly 12, information about the patient P on whom the medical procedure is to be or is being performed, other information, or a combination thereof. In some cases, the display system 17 presents confidential patient information.

The medical system 10 also includes a control system 20. The control system 20 includes at least one memory 24 and at least one processor 22 for effecting control between the medical instrument system 14, the operator input system 16, and other auxiliary systems 26 which may include, for example, imaging systems, audio systems, fluid delivery systems, display systems, illumination systems, steering control systems, irrigation systems, and/or suction systems. In one or more embodiments, the display system 17 may be in communication with the control system 20. For example, the display system 17 may be coupled to or considered one of the auxiliary systems 26 of the control system 20. A clinician C may circulate within the surgical environment 11 and may access, for example, the assembly 12 during a set up procedure or view a display of the auxiliary system 26 from the patient bedside.

Though depicted as being external to the assembly 12 in FIG. 1A, the control system 20 may, in some embodiments, be contained wholly within the assembly 12. The control system 20 also includes programmed instructions (e.g., stored on a non-transitory, computer-readable medium) to implement some or all of the methods described in accordance with aspects disclosed herein. While the control system 20 is shown as a single block in the simplified schematic of FIG. 1A, the control system 20 may include two or more data processing circuits with one portion of the processing optionally being performed on or adjacent the assembly 12, another portion of the processing being performed at the operator input system 16, and the like.

Any of a wide variety of centralized or distributed data processing architectures may be employed. Similarly, the programmed instructions may be implemented as a number of separate programs or subroutines, or they may be integrated into a number of other aspects of the systems described herein, including teleoperational systems. In one embodiment, the control system 20 supports wireless communication protocols such as Bluetooth, IrDA, HomeRF, IEEE 802.11, DECT, and Wireless Telemetry.

The control system 20 is in communication with a database 27 which may store one or more clinician profiles, a list of patients and patient profiles, a list of procedures to be performed on said patients, a list of clinicians scheduled to perform said procedures, other information, or combinations thereof. A clinician profile may comprise information about a clinician, including how long the clinician has worked in the medical field, the level of education attained by the clinician, the level of experience the clinician has with the medical system 10 (or similar systems), or any combination thereof.

The database 27 may be stored in the memory 24 and may be dynamically updated. Additionally or alternatively, the database 27 may be stored on a device such as a server or a portable storage device that is accessible by the control system 20 via an internal network (e.g., a secured network of a medical facility or a teleoperational system provider) or an external network (e.g. the Internet). The database 27 may be distributed throughout two or more locations. For example, the database 27 may be present on multiple devices which may include the devices of different entities and/or a cloud server. Additionally or alternatively, the database 27 may be stored on a portable user-assigned device such as a computer, a mobile device, a smart phone, a laptop, an electronic badge, a tablet, a pager, and other similar user devices.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, assembly 12. In some embodiments, the servo controller and assembly 12 are provided as part of a teleoperational arm cart positioned adjacent to the patient's body.

The control system 20 can be coupled with the endoscopic imaging system 15 and can include a processor to process captured images for subsequent display, such as to a surgeon on the surgeon's control console, or on another suitable display located locally and/or remotely. For example, where a stereoscopic endoscope is used, the control system 20 can process the captured images to present the surgeon with coordinated stereo images of the surgical site. Such coordination can include alignment between the opposing images and can include adjusting the stereo working distance of the stereoscopic endoscope.

In alternative embodiments, the medical system 10 may include more than one assembly 12 and/or more than one operator input system 16. The exact number of assemblies 12 will depend on the surgical procedure and the space constraints within the operating room, among other factors. The operator input systems 16 may be collocated or they may be positioned in separate locations. Multiple operator input systems 16 allow more than one operator to control one or more assemblies 12 in various combinations. The medical system 10 may also be used to train and rehearse medical procedures.

FIG. 1B is a perspective view of one embodiment of an assembly 12 which may be referred to as a patient side cart, surgical cart, teleoperational arm cart, or surgical robot. The assembly 12 shown provides for the manipulation of three surgical tools 30*a*, 30*b*, 30*c* (e.g., medical instrument systems 14) and an imaging device 28 (e.g., endoscopic imaging system 15), such as a stereoscopic endoscope used for the capture of images of the site of the procedure. The imaging device may transmit signals over a cable 56 to the control system 20. Manipulation is provided by teleoperative mechanisms having a number of joints. The imaging device 28 and the surgical tools 30*a-c* can be positioned and manipulated through incisions in the patient so that a kinematic remote center is maintained at the incision to minimize the size of the incision. Images of the surgical site can include images of the distal ends of the surgical tools 30*a-c* when they are positioned within the field-of-view of the imaging device 28.

The assembly 12 includes a drivable base 58. The drivable base 58 is connected to a telescoping column 57, which allows for adjustment of the height of arms 54. The arms 54 may include a rotating joint 55 that both rotates and moves up and down. Each of the arms 54 may be connected to an orienting platform 53. The arms 54 may be labeled to facilitate trouble shooting. For example, each of the arms 54 may be emblazoned with a different number, letter, symbol, other identifier, or combinations thereof. The orienting platform 53 may be capable of 360 degrees of rotation. The assembly 12 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument, e.g., one of the surgical tools 30*a-c*. The manipulator arms 51 may be teleoperatable. In some examples, the arms 54 connecting to the orienting platform 53 may not be teleoperatable. Rather, such arms 54 may be positioned as desired before the surgeon S begins operation with the teleoperative components. Throughout a surgical procedure, medical instruments may be removed and replaced with other instruments such that instrument to arm associations may change during the procedure.

Endoscopic imaging systems (e.g., endoscopic imaging system 15 and imaging device 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" design in which a distal digital sensor such as a one or more charge-coupled device (CCD) or a complementary metal oxide semiconductor (CMOS) device store image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle and shaft all rigidly coupled and hermetically sealed.

In the present example, the assembly 12 also includes a display device 60 of the display system 17 removably coupled to the orienting platform 53. The display device 60 may be detachable from the orienting platform 53. The display device 60 may display, for example, images provided by the endoscopic imaging system 15 in association with confidential information, such as confidential patient information. The mobile device 204 described in FIG. 2 below may be used in conjunction with the medical system 10 to protect selected information, including confidential information, that is presented on the one or more displays of the display system 17 such that the selected information is not included on captured images of the one or more displays of the display system 17.

FIG. 1C is a perspective view of an embodiment of the operator input system 16 at the surgeon's control console. The operator input system 16 includes a left eye display 32 and a right eye display 34 for presenting the surgeon S with a coordinated stereo view of the surgical environment that enables depth perception. The left and right eye displays 32, 32 may be components of the display system 17. The operator input system 16 further includes one or more input control devices 36, which in turn cause the assembly 12 to manipulate one or more instruments of the endoscopic imaging system 15 and/or medical instrument system 14. The input control devices 36 can provide the same degrees of freedom as their associated instruments to provide the surgeon S with telepresence, or the perception that the input control devices 36 are integral with said instruments so that the surgeon has a strong sense of directly controlling the instruments. To this end, position, force, and tactile feedback sensors (not shown) may be employed to transmit position, force, and tactile sensations from the medical instruments, e.g., surgical tools 30*a-c*, or imaging device 28, back to the surgeon's hands through the input control devices 36. Input control devices 37 are foot pedals that receive input from a user's foot. Aspects of the operator input system 16, the assembly 12, and the auxiliary systems 26 may be adjustable and customizable to meet the physical needs, skill level, or preferences of the surgeon S.

FIG. 1D is a top view of another embodiment of the medical system 10. In this embodiment, the medical system 10 may be a fully manual medical system that is under the direct control of the surgeon S to perform the medical procedure or sub-procedure using the medical system 10. The display device 18 may display information about the medical procedure or sub-procedure in association with confidential information, such as confidential patient information about the patient P on the operating table O. The mobile device 204 described in FIG. 2 below may be used in conjunction with the medical system 10 to protect selected information, including confidential information, that is presented on the display device 18. In some embodiments, the selected information on the display device 18 may be obscured such that taking an image of the display device 18 using the mobile device 204 will produce an image with blurred or otherwise obscured regions where the selected information is displayed. In this manner, the mobile device 204 and the display device 18 may be used together to ensure that the selected information is not included on captured images of the display device 18.

FIG. 2 is a schematic diagram of an environment 200 in which a medical procedure may be performed. In one embodiment, the environment 200 is an operating room (e.g. the surgical environment 11 of FIG. 1A). In other embodiments, the environment 200 may be an emergency room, a training environment, a medical laboratory, or some other type of environment in which any number of medical procedures or medical training procedures may take place.

A medical system 202 and a mobile device 204 are located within the environment 200. In one or more embodiments, the mobile device 204 may communicate with the medical system 202 using at least one wireless communications link. In other embodiments, the mobile device 204 may communicate using at least one wired communications link, at least one optical communications link, or both in addition to or instead of the at least one wireless communications link.

The medical system 202 may be used to perform a medical procedure, simulate a medical procedure, or both. In some embodiments, the medical system 202 may be implemented using the medical system 10 of FIG. 1A. In some embodiments, the medical system 202 described in FIG. 2 may be implemented using a medical imaging system, such as, for example, a magnetic resonance imaging (MRI) system, a computed tomography (CT) scanner system, an X-ray system, an ultrasound system, or some other type of system.

The medical system 202 includes at least one processor 206 and at least one display system 208. The processor 206 may be coupled to the display system 208. In other embodiments, the display system 208 may be considered separate from the medical system 202 but in communication with the processor 206. The processor 206 may be used to run executable code stored on memory to simulate or perform a medical procedure. In some embodiments, the processor 206 may be implemented using the processor 22 of the control system 20 in FIG. 1A.

The display system 208 may include one or more display devices communicatively coupled to the processor 206. For example, the display system 208 may include a display device 210 that is communicatively coupled to the processor 206 and that visually presents a display 212. The display device 210 may take the form of a monitor, a touchscreen display device, or some other type of visual output device. The display 212 may be a graphical user interface with various types of information including, but not limited to, information about the medical procedure being performed by or simulated by the medical system 202, information about the patient on whom the medical procedure is being performed or is to be performed, other information, or a combination thereof. In some embodiments, the display system 208 may be implemented using the display system 17 in FIG. 1.

At some point during a medical procedure (a real or simulated medical procedure), an operator may desire to capture what is visible on the display 212 presented by the display device 210, but it may be necessary to prevent selected information 214 from being captured and stored. Selected information 214 may include any type of information that the operator does not want to capture or that the operator should not be able to capture. As one example, the selected information 214 may include confidential information 216. For example, the selected information may include information considered confidential under the Health Insurance Portability and Accountability Act (HIPAA). The confidential information 216 may include at least one of a first name, a last name, a birthday, an age, medical history information, a patient identification number, a social security number, or some other piece of confidential information. The confidential information 216 may be specific to the patient. In some embodiments, the selected information 214 may include other information that is not traditionally thought of as confidential information or sensitive information. For example, the selected information 214 may include a current date, a physician name, an operating room number, an image of the patient, a portion of an image, some other type of information, or a combination thereof. The selected information may be selected by an operator or may be selected based on predetermined criteria, such as HIPAA.

The mobile device 204 may take various forms. The mobile device 204 may be, for example, a smartphone, a tablet, a laptop, or some other type of portable device. The portable device may include an imaging device, such as a camera or video recording device.

The mobile device 204 may be used to initiate the creation of a final image 218 that captures the display 212 on the display device 210 but does not include the selected information 214. The mobile device 204 includes at least one processor 220. The processor 220 may be used to run executable code stored on memory to initiate the creation of the final image 218. When an operator desires to capture the display 212, the mobile device 204 may be used to generate a trigger 221 that is sent to the medical system 202 and used to initiate the creation of the final image 218. In one embodiment, the processor 220 may run executable code stored on memory to launch an application 222 that is used to generate and send the trigger 221 to thereby initiate the creation of the final image 218. In some embodiments, the application 222 may be used to generate the final image 218. In other embodiments, the application 222 may be used to initiate the generation of the final image 218 by the medical system 202.

Figure 3:
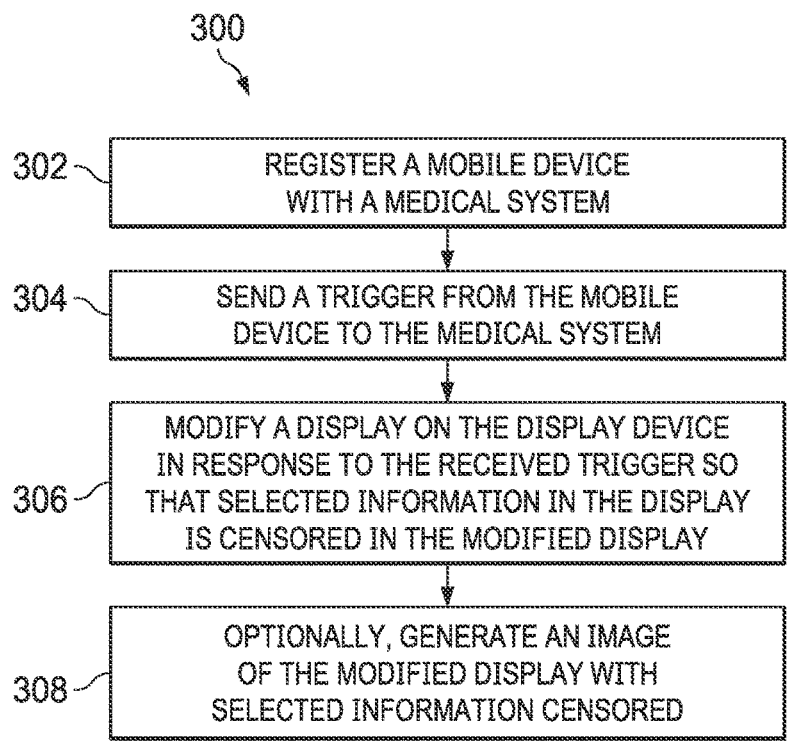
FIG. 3 is a flowchart illustrating a method for controlling information captured in an image, in accordance with an embodiment.

FIG. 3 is a flowchart of a method 300 for controlling information captured in an image. The method 300 is illustrated in FIG. 3 as a set of operations or processes 302 through 308 and is described with continuing reference to FIG. 2. Not all of the illustrated processes 302 through 308 may be performed in all embodiments of method 300. Additionally, one or more processes that are not expressly illustrated in FIG. 3 may be included before, after, in between, or as part of the processes 302 through 308. In some embodiments, one or more of the processes 302 through 308 may be implemented, at least in part, in the form of executable code stored on non-transitory, tangible, machine-readable media that when run by one or more processors (e.g., the processors of control system) may cause the one or more processors to perform one or more of the processes.

At process 302, which may be optional, the mobile device 204 is registered with the medical system 202. The registration may occur using a wireless communications link. In one or more embodiments, registration of the mobile device 204 with the medical system 202 may include a network handshake between the mobile device 204 and the medical system 202. For example, the mobile device 204 may connect to a same private or secure wireless network to which the medical system 202 is connected. In some embodiments, this connection may be considered the registration of the mobile device 204 with the medical system 202. In certain embodiments, the mobile device 204 and the medical system 202 may communicate through an intermediary device connected to the private or secure wireless network. The intermediary device may be, for example, a server or other intermediary device functioning as a router. Registering the mobile device 204 with the medical system 202 may thus include the server authenticating the mobile device 204 before allowing the exchange of information between the mobile device 204 and the medical system 202.

In other embodiments, registering the mobile device 204 with the medical system 202 may allow the medical system 202 to authenticate or otherwise validate the mobile device 204. For example, the medical system 202 may be preset to only accept commands, signals, or notifications from preauthorized mobile devices or preauthorized operators.

In some embodiments, registering the mobile device 204 may include sending authorization information to the medical system 202. The authorization information may include, for example, identification information for the operator of the mobile device 204, identification information for the mobile device 204, a code, a pin number, or a combination thereof.

In one example, launching the application 222 on the mobile device 204 may automatically initiate the registration and cause the authorization information to be sent to the medical system 202. In another example, the operator selecting a particular graphical feature on a graphical user interface of a display on the mobile device 204 causes the authorization information to be sent to the medical system 202. The registration may also include the medical system 202 validating the mobile device 204 or the operator of the mobile device based on the authorization information.

At process 304, the trigger 221 is sent from the mobile device 204 to the medical system 202. The trigger may be sent using a wireless communications link. The trigger 221 may be a command, a signal, a notification, or some other type of information. In these embodiments, the trigger 221 may only be sent from the mobile device 204 upon registration of the mobile device 204 with the medical system 202.

At process 306, the display 212 on the display device 210 is modified in response to receiving the trigger from the mobile device 204. The modifications to the display 212 include censoring selected information 214. The selected information 214 may be considered censored when the selected information 214 is not visible, apparent, or otherwise visually or readily discernible in the modified display. In one or more embodiments, modifying the display 212 includes obscuring a region of the display 212 that presents the selected information 214 in response to receiving the trigger 221 such that the final image 218 of the display 212 will include the obscured region. In some embodiments, the region that is obscured may be comprised of multiple discontinuous sub-regions.

At process 308, which may be optional, an image is generated of the modified display with the selected information censored. In one embodiment, the generated image may be the final image 218 generated by the mobile device 204. The final image 218 may be stored for later use. In another embodiment, the image may be an image (e.g., a photo, a video, or an image in a portable document format (PDF)) generated by the medical system. The generated image may be stored on the mobile device 204, the medical system 202, or both. In other embodiments, the generated image may be stored in cloud memory.

Figure 4:
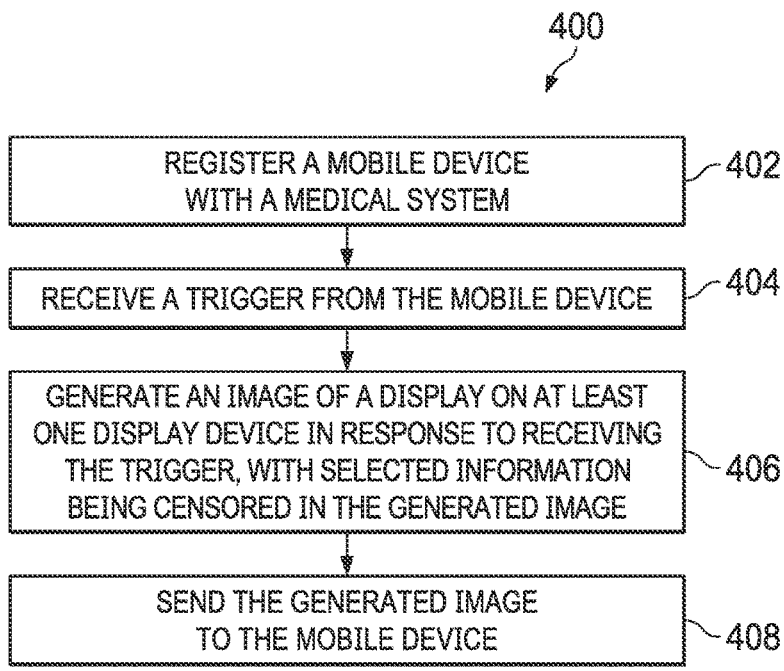
FIG. 4 is a flowchart illustrating a method for censoring selected information, in accordance with an embodiment.

FIG. 4 is an illustration of a method 400 for censoring selected information in an environment. The method 400 is illustrated as a set of operations or processes 402 through 408 and is described with continuing reference to FIG. 2. Not all of the illustrated processes 402 through 408 may be performed in all embodiments of method 400. Additionally, one or more processes that are not expressly illustrated in FIG. 4 may be included before, after, in between, or as part of the processes 402 through 408. In some embodiments, one or more of the processes 402 through 408 may be implemented, at least in part, in the form of executable code stored on non-transitory, tangible, machine-readable media that when run by one or more processors (e.g., the processors of control system) may cause the one or more processors to perform one or more of the processes. In one or more embodiments, the processes 402 through 408 may be performed by the medical system 202.

At process 402, the mobile device 204 is registered with the medical system 202 using, for example, a wireless communications link established between the mobile device 204 and the medical system 202. In some embodiments, the process 402 may include the medical system 202 authenticating the mobile device 204 as part of or in addition to registering the mobile device 204 with the medical system 202. At process 404, the trigger 221 is received from the mobile device 204 over, for example, the wireless communications link.

At process 406, an image of the display 212 on the display device 210 is generated in response to receiving the trigger 221, with selected information being censored in the generated image. For example, the medical system 202 may generate a screenshot or screen capture of the display 212. Censoring the selected information 214 means ensuring that the final image 218 does not make the selected information 214 visible, apparent, or otherwise discernible. The selected information 214 may be censored by, for example, concealing the selected information 214 in the image, removing the selected information from the image, encrypting the selected information in the image, obscuring the selected information in the image, or a combination thereof to produce a censored image. In some cases, this censoring of the selected information 214 may also be referred to as redacting the selected information 214. Optionally, the medical system may create a preliminary image that may include the selected information 214, and may then modify the preliminary image to generate a secondary or final image that has the selected information censored.

In some embodiments, the medical system 202 may encrypt or otherwise secure the selected information 214 in the preliminary image such that final image 218 is an encrypted image. For example, the medical system 202 may encrypt the selected information 214 in the preliminary image using a password or a code that would only be available on the mobile device 204 that belongs to an authorized operator or clinician.

For example, the medical system 202 may alter the color values of pixels within or pixelate a block or region of the preliminary image that includes the selected information 214. In other examples, the medical system 202 may encrypt the text presenting the selected information 214. In still other examples, the medical system 202 may blur a portion of the preliminary image that includes at least a portion of the selected information.

At process 408, which may be optional, the generated censored image is sent to the mobile device 204 as the final image 218. The final image 218 does not include the selected information 214. In some embodiments, the selected information 214 includes the confidential information 216. As one specific example, the confidential information 216 may be information that is considered confidential according to certain regulatory, legal, and/or ethical standards. For example, the confidential information 216 may be information that is considered confidential under the Health Insurance Portability and Accountability Act (HIPAA) of 1996. By censoring this confidential information 216, the medical system 202 ensures that later use and/or storage of the final image 218 will not violate HIPAA regulations and/or other confidentiality compliance requirements.

Figure 5:
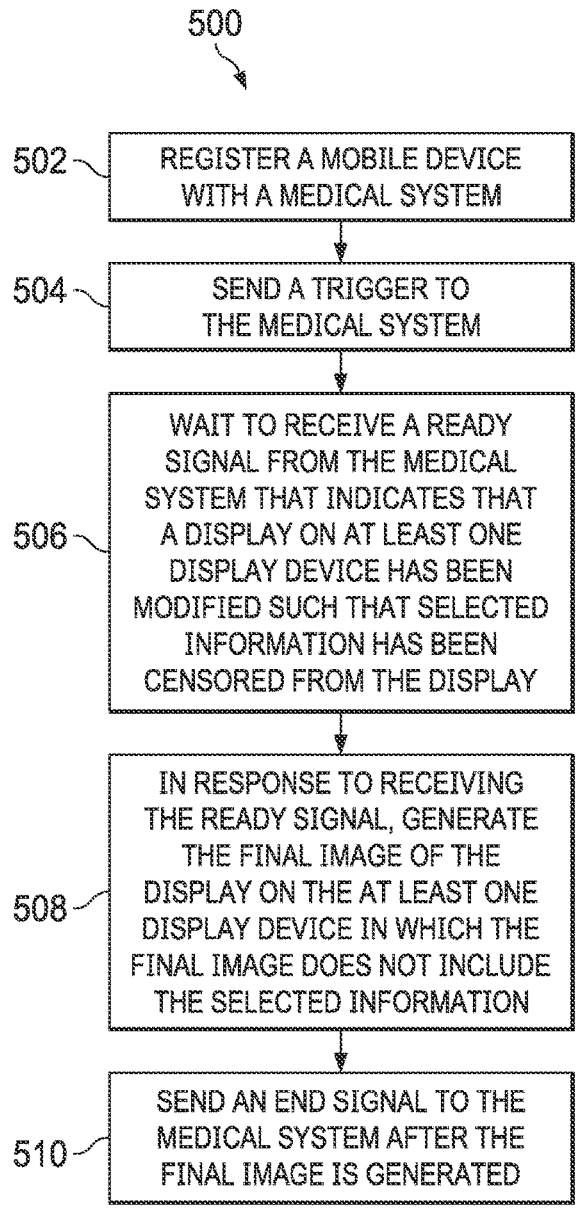
FIG. 5 is a flowchart illustrating a method for censoring selected information, in accordance with an embodiment.

FIG. 5 is an illustration of a method 500 for censoring selected information in an environment. The method 500 is illustrated as a set of operations or processes 502 through 510 and is described with continuing reference to FIG. 2. Not all of the illustrated processes 502 through 510 may be performed in all embodiments of method 500. Additionally, one or more processes that are not expressly illustrated in FIG. 5 may be included before, after, in between, or as part of the processes 502 through 510. In some embodiments, one or more of the processes 502 through 510 may be implemented, at least in part, in the form of executable code stored on non-transitory, tangible, machine-readable media that when run by one or more processors (e.g., the processors of control system) may cause the one or more processors to perform one or more of the processes. In one or more embodiments, the processes 502 through 510 may be performed by the mobile device 204.

At process 502, the mobile device 204 is registered with the medical system 202 using, for example, a wireless communications link established between the mobile device 204 and the medical system 202. At process 504, the trigger 221 is sent to the medical system 202 over, for example, the wireless communications link.

At process 506, the mobile device 204 waits to receive a ready signal from the medical system 202 that indicates that the display 212 on the at least one display device 210 has been modified such that the selected information 214 has been censored from the display 212. The medical system 202 may have modified the display 212 by removing the selected information 214 from the display 212, obscuring the selected information 214, concealing the selected information 214, encrypting the selected information 214, or otherwise altering the selected information 214 or the display 212. Obscuring the selected information 214 may include pixelating a region or portion of the display 212 that includes the selected information 214.

At process 508, in response to receiving the ready signal, the mobile device 204 generates the final image 218 of the display 212 on the at least one display device 210 in which the final image 218 does not include the selected information 214. When the selected information 214 includes the confidential information 216, the final image 218 may then be used or stored without concerns that such use or storage violates certain regulatory, legal, and/or ethical standards or requirements. The final image 218 may be stored on the mobile device 204, sent back to the medical system 202, stored in cloud memory, or a combination thereof. In other embodiments, the mobile device 204 may begin recording a video upon receiving the ready signal.

At process 510, which may be optional, the mobile device 204 sends an end signal to the medical system 202 after the final image 218 is generated. The end signal alerts the medical system 202 that the selected information 214 previously censored from the display 212 may now be restored. The selected information 214 is uncensored in the restored display 212. In other words, the medical system 202 may now uncensor the selected information 214 by adding back the selected information 214 to the display 212, decrypting the selected information 214, or otherwise revealing the selected information 214.

In other embodiments, the medical system 202 may not censor all of the selected information 214 on the display 212 before sending the ready signal to the mobile device 204. For example, the mobile device 204 may generate a preliminary image that is partially censored. The mobile device 204 may then censor the remaining portion of the selected information 214 to produce the final image 218.

Figure 6:
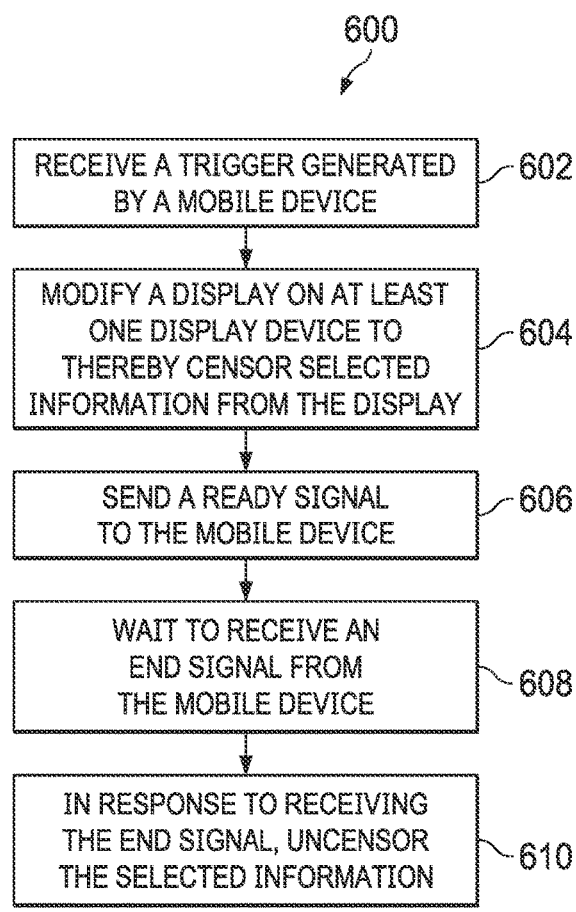
FIG. 6 is a flowchart illustrating a method for censoring selected information, in accordance with an embodiment.

FIG. 6 is an illustration of a method 600 for censoring selected information in an environment. The method 600 is illustrated as a set of operations or processes 602 through 610 and is described with continuing reference to FIG. 2. Not all of the illustrated processes 602 through 610 may be performed in all embodiments of method 600. Additionally, one or more processes that are not expressly illustrated in FIG. 6 may be included before, after, in between, or as part of the processes 602 through 610. In some embodiments, one or more of the processes 602 through 610 may be implemented, at least in part, in the form of executable code stored on non-transitory, tangible, machine-readable media that when run by one or more processors (e.g., the processors of control system) may cause the one or more processors to perform one or more of the processes. In one or more embodiments, the processes 602 through 610 may be performed by the medical system 202.

At process 602, the medical system 202 receives a trigger 221 generated by the mobile device 204. The trigger 221 may be received directly from the mobile device 204 or from a server or router on the same private or secure wireless network as the medical system 202. For example, the mobile device 204 may be connected to the same private or secure wireless network and may have been authenticated by the server or router prior to the mobile device 204 generating and sending the trigger 221. In other embodiments, the trigger 221 may itself be an alert or notification indicating that the mobile device 204 has been authenticated.

At process 604, the display 212 on the at least one display device 210 is modified to thereby censor the selected information 214 from the display 212. The medical system 202 may modify the display 212 by removing the selected information 214 from the display 212, obscuring the selected information 214, concealing the selected information 214, encrypting the selected information 214, or otherwise altering the selected information 214 or the display 212. At process 606, a ready signal is sent to the mobile device 204. In some embodiments, the process 606 includes sending the ready signal to a server or router, which then sends the signal to the mobile device 204.

At process 608, the medical system 202 waits to receive an end signal from the mobile device 204. The end signal may be received directly from the mobile device 204 or from the server or router in communication with the mobile device 204. At process 610, in response to receiving the end signal, the medical system 202 uncensors the selected information 214. Uncensoring the selected information 214 in response to the received end signal may include undoing or reversing any actions taken to censor the selected information 214.

Figure 7:
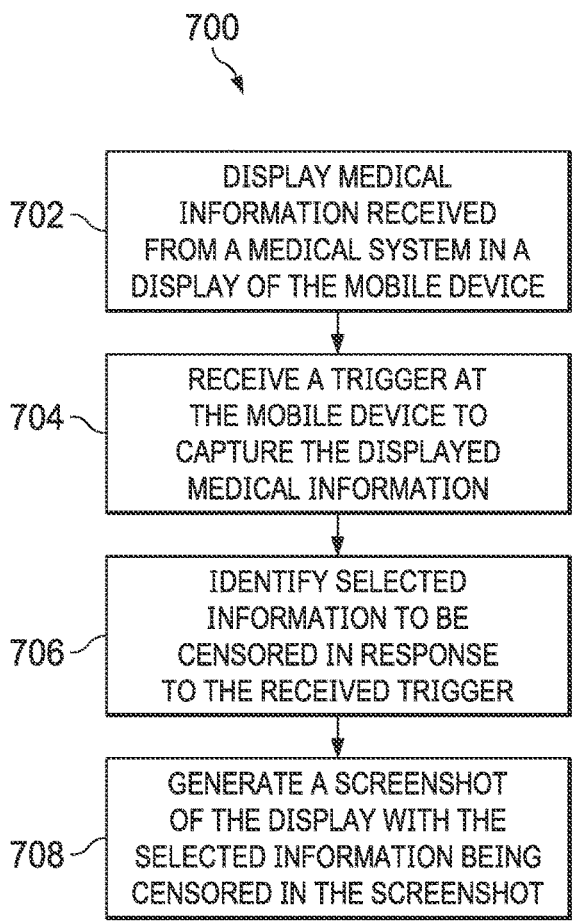
FIG. 7 is a flowchart illustrating a method for capturing a screenshot, in accordance with an embodiment.

FIG. 7 is a flowchart illustrating a method for capturing a screenshot. The method 700 is illustrated as a set of operations or processes 702 through 708 and is described with continuing reference to FIG. 2. Not all of the illustrated processes 702 through 708 may be performed in all embodiments of method 700. Additionally, one or more processes that are not expressly illustrated in FIG. 7 may be included before, after, in between, or as part of the processes 702 through 708. In some embodiments, one or more of the processes 702 through 708 may be implemented, at least in part, in the form of executable code stored on non-transitory, tangible, machine-readable media that when run by one or more processors (e.g., the processors of control system) may cause the one or more processors to perform one or more of the processes. In one or more embodiments, the processes 702 through 708 may be performed by the mobile device 204.

At process 702, medical information received from the medical system 202 is displayed in a display of the mobile device 204. In one or more embodiments, the mobile device 204 may belong to one of the operating staff in the environment 200. At process 704, the mobile device 204 receives a trigger 221 to capture the displayed medical information. In one or more embodiments, the trigger 221 may be generated by application 222 running on the mobile device 204. At process 706, selected information 214 to be censored is identified in response to the received trigger 221. The selected information 214 may include, for example, confidential information 216.

At process 708, a screenshot of the display is generated with the selected information 214 being censored in the screenshot. The screenshot may be, for example, final image 218. In some embodiments, process 708 includes the process of obscuring the selected information 214 displayed on the mobile device 204 in response to the received trigger 221, such that the selected information 214 is censored in the screenshot of the display. In other embodiments, the medical information displayed on the mobile device 204 is modified in response to the received trigger 221 prior to the generation of the screenshot such that the selected information 214 in the display is censored. In these embodiments, the display on the mobile device 204 may be restored after the screenshot is captured such that the selected information 214 in the restored display is uncensored. In still other embodiments, at process 708, the screenshot of the display is generated such that the selected information 214 is censored in the screenshot but is uncensored in the display.

Figure 8:
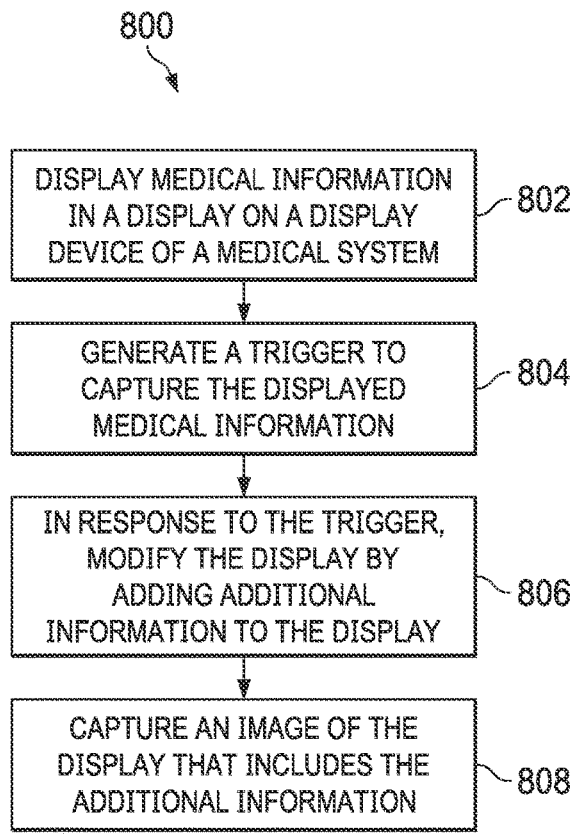
FIG. 8 is a flowchart illustrating a method for generating an image with additional information, in accordance with an embodiment.

FIG. 8 is a flowchart illustrating a method for generating an image with additional information. The method 800 is illustrated as a set of operations or processes 802 through 808 and is described with continuing reference to FIG. 2. Not all of the illustrated processes 802 through 808 may be performed in all embodiments of method 800. Additionally, one or more processes that are not expressly illustrated in FIG. 8 may be included before, after, in between, or as part of the processes 802 through 808. In some embodiments, one or more of the processes 802 through 808 may be implemented, at least in part, in the form of executable code stored on non-transitory, tangible, machine-readable media that when run by one or more processors (e.g., the processors of control system) may cause the one or more processors to perform one or more of the processes. In one or more embodiments, the processes 802 through 808 may be performed by the mobile device 204.

At process 802, medical information is displayed in a display on the display device 210 of the medical system 202. A user of the mobile device 204 may want to capture this medical information in an image or screenshot. At process 804, a trigger 221 to capture the displayed medical information is generated. This trigger 221 may be generated by, for example, an application 222 running on the mobile device 204, a program running in the medical system 202, or some other device or program.

At process 806, in response to the trigger 221, the display is modified by adding additional information to the display. The additional information may include, for example, without limitation, training information, information registered from the medical procedure (e.g., surgery), other types of information, or a combination thereof. For example, the trigger 221 may cause the display device 210 to add data that is collected by the medical system 202 but not already displayed on the display device 210 to the display. In some cases, receiving the trigger 221 at the mobile device 204 or the medical system 202 may cause user-specific information to be added to the display. In still other cases, receiving the trigger 221 at the mobile device 204 or the medical system 202 may cause codes, labels, markers, date and time information, instructions, or other types of information to be added to the display. In one or more example embodiments, the trigger 221 may result in a legend, a table, a chart, a new image, a stored image, stored endoscope position data, a hyperlink, some other type of information or data, or a combination thereof being added to the display.

In one or more example embodiments, the additional information may include information or data that, if displayed on the display device 210 during a medical procedure, would cause the display to be too cluttered or too confusing. However, capturing this type of information in an image or screenshot may be useful when looking at the image contemporaneously or when looking at the image after the medical procedure.

At process 808, an image of the display that includes the additional information is then captured. For example, the medical system 202 may send a ready signal to the mobile device 204 once the additional information has been added to the display. The mobile device 204 may then be used to capture a screenshot of the display. In some cases, the mobile device 204 then sends an end signal to the medical system 202, which causes the additional information to be removed from the display. In other example embodiments, at process 808, the medical system 202 may itself generate a screenshot of the display once the display has been modified and may then send this captured screenshot to the mobile device 204.

Thus, the display of the display device 210 may be modified in response to a trigger 221 in a variety of ways. For example, the display may be modified by censoring selected information in response to a trigger 221 as described above in other example embodiments, adding additional (e.g., relevant) information in response to a trigger 221 as discussed above with respect to process 800, or both.

In other example embodiments, the medical information displayed on the display device 210 may be sent to the mobile device 204 and displayed on the mobile device 204. In response to a trigger 221 being then received at the mobile device 204, the additional information may be added to the display of the mobile device 204. A screenshot of the display on the mobile device 204 may then be generated such that the screenshot includes the additional information. Once the screenshot has been generated, the additional information may be removed from the display on the mobile device 204.

Figure 9:
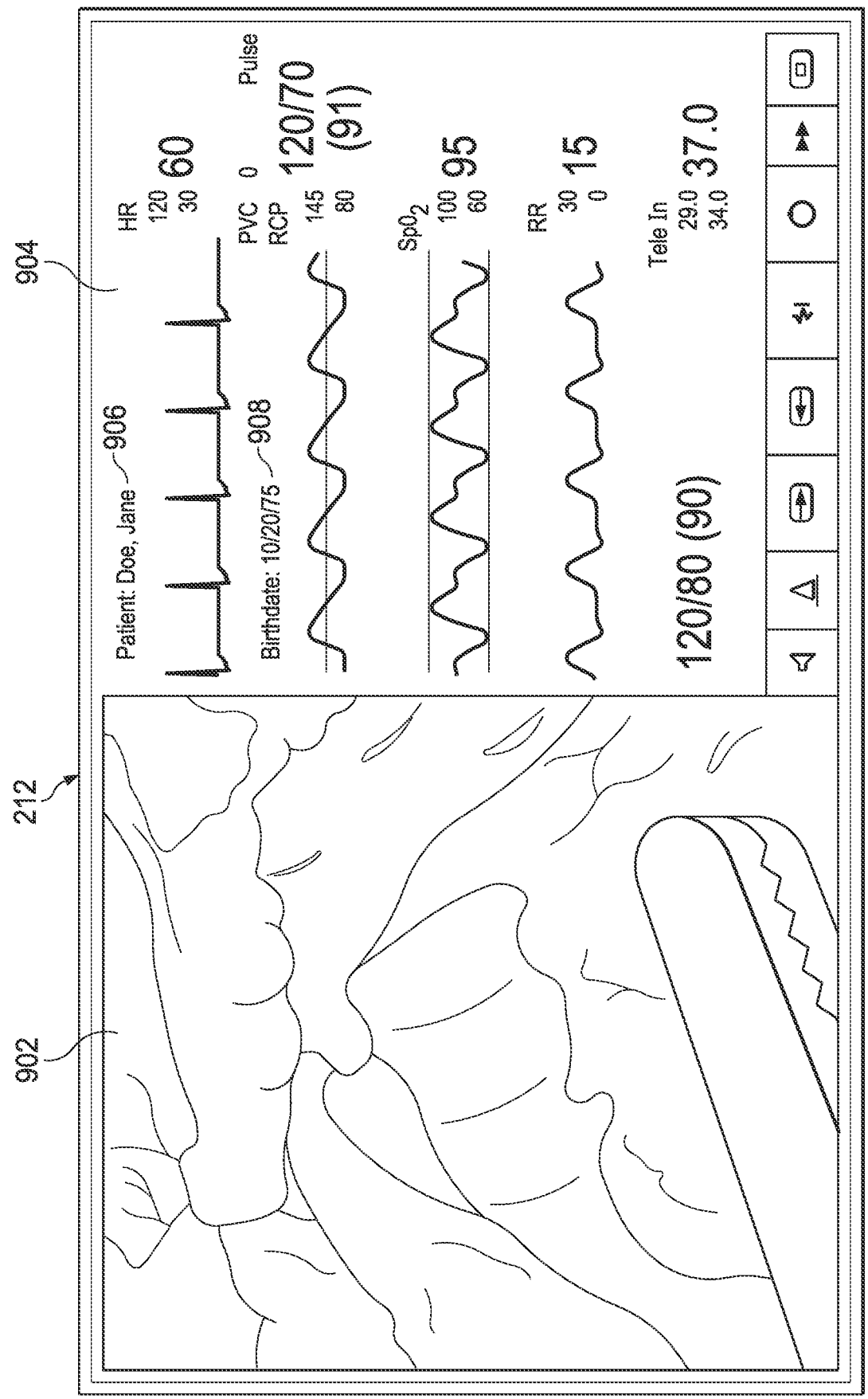
FIG. 9 is an illustration of a display presenting an image of a medical procedure and other medical information, in accordance with an embodiment.

FIG. 9 is an illustration of the display 212 presenting an image of a medical procedure and other medical information. The display 212 presents an image 902 provided by an endoscopic imaging system (e.g. endoscopic imaging system 15 in FIG. 1A). The display 212 also presents medical information 904. The medical information 904 includes confidential information 216 (i.e. confidential patient information) such as a patient name 906 and a patient birthdate 908. The medical system 202 (e.g. the medical system 10 of FIG. 1A) may modify the display 212 upon receiving the trigger 221 to remove the patient name 906 and the patient birthdate 908.

Figure 10:
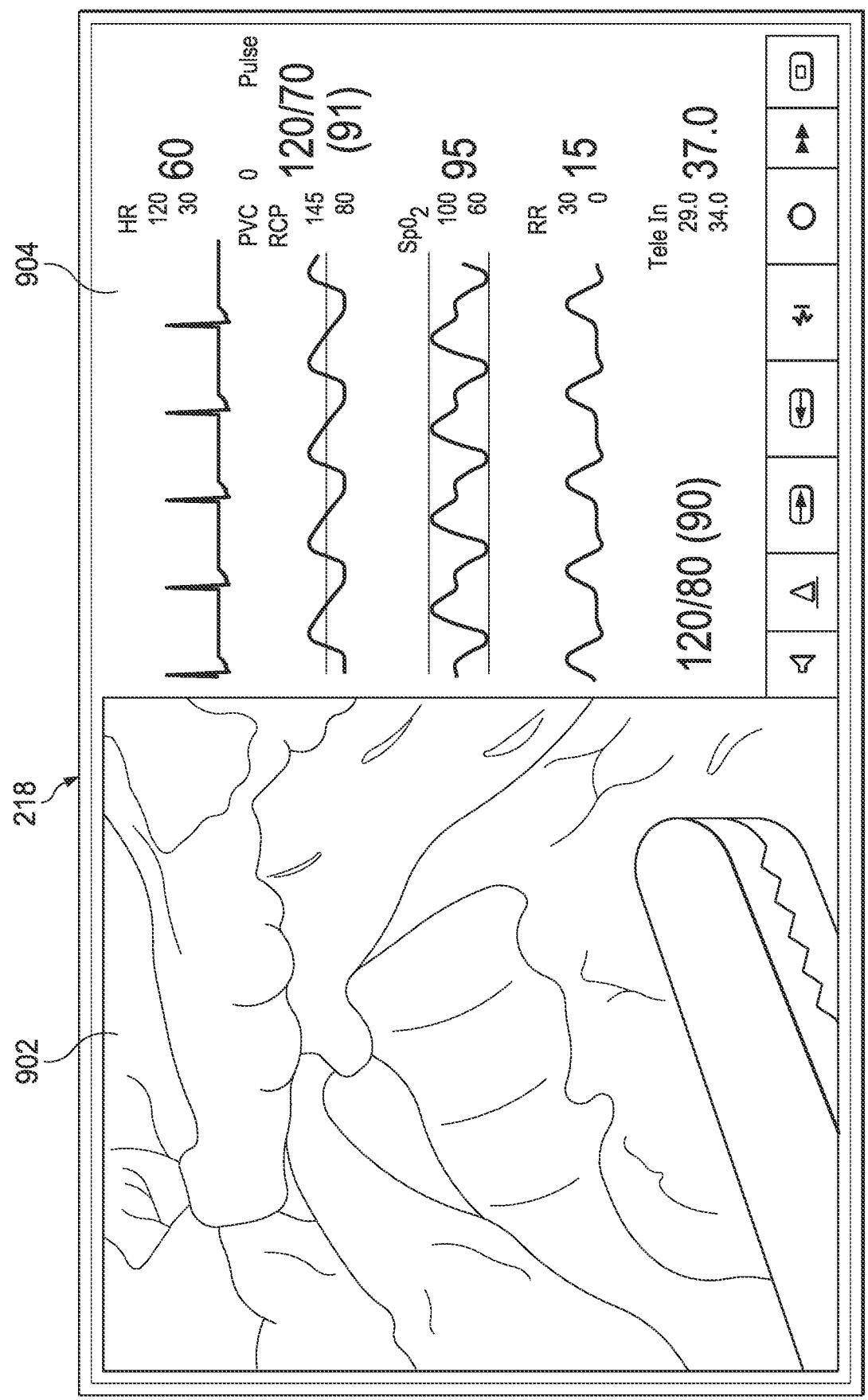
FIG. 10 is an illustration of a final image that does not include confidential information, in accordance with an embodiment.

FIG. 10 is an illustration of the final image 218 that does not include confidential information 216. As depicted, the final image 218 includes the image 902 and the medical information 904, but does not include the patient name 906 and the patient birthdate 908 of FIG. 9. Thus, the final image 218 may be considered in compliance with certain regulatory, legal, and ethical standards or requirements.

Thus, the embodiments described above provide a method and apparatus for controlling the information that is captured in an image of at least one display 212 in the environment 200 (e.g. the surgical environment 11 in FIG. 1A). The systems and methods described above may be similarly used to censor selected information 214 in video capturing at least one display 212 in the environment 200. The embodiments provide methods for easily capturing images of one or more displays presenting information about a medical procedure (e.g. a surgical case) without also capturing confidential information.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

Various aspects of the subject matter described herein are set forth in the following numbered examples.

Example 1: A method comprises registering a mobile device with a medical system, the medical system including a display device; receiving a trigger from the mobile device at the medical system; generating an image of a display on the display device with selected information censored in response to receiving the trigger; and sending the image of the display with the selected information censored to the mobile device.

Example 2: The method of example 1, wherein the trigger is received from the mobile device over a wireless communications link.

Example 3: The method of example 1, wherein the selected information is censored by concealing the selected information in the image.

Example 4: The method of example 1, wherein the selected information is censored by removing the selected information in the image.

Example 5: The method of example 1, wherein the selected information is censored by encrypting the selected information in the image.

Example 6: The method of example 1, wherein the selected information is censored by obscuring the selected information in the image.

Example 7: The method of example 1, wherein the selected information includes at least one of a name, a birthday, an age, medical history information, a patient identification number, a social security number, a current date, a physician name, or an operating room number.

Example 8: A method for capturing a screenshot comprises displaying, on a display of a mobile device, medical information received from a medical system; receiving, from the mobile device, a trigger to capture the displayed medical information; identifying selected information to be censored in response to the received trigger; and generating the screenshot of the display, wherein the selected information is censored in the screenshot.

Example 9: The method of example 8, further comprising modifying the medical information displayed on the mobile device in response to the received trigger such that the selected information in the display is censored.

Example 10: The method of example 8, wherein generating the screenshot comprise s obscuring the selected information displayed on the mobile device in response to the received trigger such that the selected information is censored in the screenshot of the display.

Example 11: The method of example 10, further comprising restoring the display on the mobile device after the screenshot is captured such that the selected information in the restored display is uncensored.

Example 12: The method of example 8, wherein generating the screenshot comprises generating the screenshot of the display such that the selected information is censored in the screenshot but is uncensored in the display.

Example 13: A mobile device that comprises a display; and a processor configured to display medical information received from a medical system in the display; receive a trigger to capture the displayed medical information; identify selected information to be censored in response to the received trigger; and generate a screenshot of the display, wherein the selected information is censored in the screenshot.

Example 14: The mobile device of example 13, wherein the processor is further configured to modify the medical information in the display in response to the received trigger such that the selected information in the display is censored.

Example 15: The mobile device of example 13, wherein the processor is further configured to obscure the selected information in the display in response to the received trigger such that the selected information is censored in the screenshot of the display.

Example 16: The mobile device of example 15, wherein the processor is further configured to restore the display on the mobile device after the screenshot is captured such that the selected information in the restored display is uncensored.

Example 17: The mobile device of example 13, wherein the processor is further configured to generate the screenshot of the display such that the selected information is censored in the screenshot but is uncensored in the display.

Example 18: A method of obscuring selected information comprises displaying medical information in a display on a display device of a medical system; receiving a trigger from the mobile device at the medical system; and obscuring a region of the display that presents the selected information in response to receiving the trigger such that an image of the display device includes the obscured region.

Example 19: The method of example 18, further comprising generating the image of the display device using the mobile device, wherein the image includes the obscured region.

Example 20: The method of example 18, further comprising registering the mobile device with the medical system prior to the mobile device sending the trigger to the medical system.

Example 21: The method of example 18, wherein the selected information includes confidential information and wherein the region of the display includes multiple discontinuous sub-regions.

Example 22: A method for modifying a display on a display device of a medical system comprises displaying medical information in the display on the display device of the medical system; receiving a trigger from the mobile device at the medical system; and adding additional information on the display in response to receiving the trigger such that an image of the display device includes the additional information.

Example 23: The method of example 22, wherein the additional information includes at least one of training information, codes, labels, markers, surgical information, or date and time information.

What is claimed is:

1. A medical system comprising:
a display device; and
a processor configured to perform operations including:
register a mobile device, wherein the mobile device is separate from the display device;
receive a trigger from the mobile device;
modify a display on the display device in response to the received trigger, wherein selected information is censored in the modified display;
receive an end signal from the mobile device after the mobile device has generated an image of the modified display; and
in response to receiving the end signal, restore the display on the display device, wherein the selected information is uncensored in the restored display.

2. The medical system of claim 1, wherein the processor is further configured to send the image of the modified display, with the selected information censored, to the mobile device.

3. The medical system of claim 1, wherein the trigger is received from the mobile device over a wireless communications link.

4. The medical system of claim 1, wherein the selected information is censored by at least one of concealing, removing, encrypting, or obscuring the selected information in the modified display.

5. The medical system of claim 1, wherein the end signal from the mobile device indicates that the mobile device has generated the image of the modified display.

6. The medical system of claim 1, wherein the selected information includes at least one of a name, a birthday, an age, medical history information, a patient identification number, a social security number, a current date, a physician name, or an operating room number.

7. The medical system of claim 1, wherein the processor is further configured to send a ready signal to the mobile device indicating that the selected information is censored in the modified display.

8. The medical system of claim 7, wherein the ready signal initiates generation of the image of the modified display by the mobile device.

9. The medical system of claim 1, wherein generating the image of the modified display includes capturing the modified display using an imaging element of the mobile device.

10. The medical system of claim 1, wherein receiving the trigger indicates that an operator desires to capture the display, wherein the trigger is generated by an application running on the mobile device, and wherein the trigger can only be received from the mobile device after the mobile device is registered.

11. A system comprising:
a display device;
a processor; and
a memory having computer readable instructions stored thereon, wherein the computer readable instructions, when executed by the processor, cause the system to perform operations including:
register a mobile device, wherein the mobile device is separate from the display device;
receive a trigger from the mobile device;
modify a display on the display device in response to the received trigger, wherein selected information is censored in the modified display;
receive an end signal from the mobile device after the mobile device has generated an image of the modified display; and
in response to receiving the end signal, restore the display on the display device, wherein the selected information is uncensored in the restored display.

12. The system of claim 11, wherein the computer readable instructions, when executed by the processor, further cause the system to communicate the image of the modified display to the mobile device.

13. The system of claim 11, wherein the computer readable instructions, when executed by the processor, further cause the system to receive the trigger from the mobile device over a wireless communications link.

14. The system of claim 11, wherein the computer readable instructions, when executed by the processor, further cause the system to censor the selected information in the display by at least one of concealing, removing, encrypting, or obscuring the selected information in the modified display.

15. The system of claim 11, wherein the selected information includes at least one of a name, a birthday, an age, medical history information, a patient identification number, a social security number, a current date, a physician name, or an operating room number.

16. A method comprising:
registering a mobile device with a medical system, the medical system including a display device, wherein the mobile device is separate from the display device;
receiving a trigger from the mobile device at the medical system;
modifying a display on the display device in response to the received trigger, wherein selected information in the display is censored in the modified display;
receiving an end signal from the mobile device after the mobile device has generated an image of the modified display; and
in response to receiving the end signal, restoring the display on the display device, wherein the selected information is uncensored in the restored display.

17. The method of claim 16, further comprising:
communicating the image of the modified display to the mobile device.

18. The method of claim 16, wherein the trigger is received from the mobile device over a wireless communications link.

19. The method of claim 16, wherein the selected information in the display is censored by concealing, removing, encrypting, or obscuring the selected information in the modified display.

20. The method of claim 16, wherein the selected information includes at least one of a name, a birthday, an age, medical history information, a patient identification number, a social security number, a current date, a physician name, or an operating room number.

* * * * *